(12) United States Patent
Spain et al.

(10) Patent No.: US 12,109,144 B2
(45) Date of Patent: Oct. 8, 2024

(54) OSTOMY ATTACHMENTS

(71) Applicant: OSTOFORM LIMITED, Westmeath (IE)

(72) Inventors: Eoghan Spain, Westmeath (IE); Kevin Kelleher, Westmeath (IE)

(73) Assignee: OSTOFORM LIMITED, Westmeath (IE)

( * ) Notice: Subject to any disclaimer, the term of this patent is extended or adjusted under 35 U.S.C. 154(b) by 161 days.

(21) Appl. No.: 17/058,569

(22) PCT Filed: Jun. 3, 2019

(86) PCT No.: PCT/EP2019/064295
§ 371 (c)(1),
(2) Date: Nov. 24, 2020

(87) PCT Pub. No.: WO2019/229267
PCT Pub. Date: Dec. 5, 2019

(65) Prior Publication Data
US 2021/0205117 A1    Jul. 8, 2021

(30) Foreign Application Priority Data
Jun. 1, 2018 (GB) ...................................... 1809053

(51) Int. Cl.
*A61F 5/443* (2006.01)
*A61F 5/44* (2006.01)

(52) U.S. Cl.
CPC ............ *A61F 5/443* (2013.01); *A61F 5/4404* (2013.01)

(58) Field of Classification Search
CPC .................... A61F 5/443; A61F 5/4404; A61F 2005/4486; A61F 2005/4483; A16F 5/448; A16F 5/4407; A16F 5/4408; A16F 5/443
See application file for complete search history.

(56) References Cited

U.S. PATENT DOCUMENTS 9,750,633 B1 * 9/2017 Follenius ................ A61F 5/443
2002/0088080 A1  7/2002 Fenton
(Continued)

FOREIGN PATENT DOCUMENTS

| EP | 0 197 672 A2 | 10/1986 |
| WO | 98/53772 A1 | 12/1998 |
| WO | 2017/167582 A2 | 10/2017 |

OTHER PUBLICATIONS

International Search Report and Written Opinion for corresponding Application No. PCT/EP2019/064295 (mailed Jan. 3, 2020).
(Continued)

*Primary Examiner* — Benjamin J Klein
*Assistant Examiner* — Rachel O'Connell
(74) *Attorney, Agent, or Firm* — Troutman Pepper Hamilton Sanders LLP (Rochester)

(57) ABSTRACT

An ostomy attachment including: a flexible annular seal configured to at least partially surround a stoma, the flexible annular seal including a first face and a second face; wherein the first face and the second face are bounded by an inner rim and an outer rim, wherein the inner rim is concentrically arranged within the outer rim; and an ostomy seal liner configured to engage with the inner rim of the flexible annular seal; wherein the ostomy seal liner includes one or more stabilising extensions, wherein the one or more stabilising extensions extend from the ostomy seal liner radially outward and over the first face of the flexible annular seal; and wherein the one or more stabilising extensions are in contacting relation with the first face of the flexible annular seal. Methods of manufacturing ostomy attachments and methods of use are also provided.

19 Claims, 4 Drawing Sheets

(56) References Cited

U.S. PATENT DOCUMENTS

| | | | |
|---|---|---|---|
| 2015/0305916 A1* | 10/2015 | Hanuka | A61F 5/441 |
| | | | 604/335 |
| 2017/0156920 A1* | 6/2017 | Hunt | A61F 5/445 |
| 2017/0231802 A1* | 8/2017 | Luce | A61F 5/448 |
| | | | 604/335 |
| 2018/0055679 A1* | 3/2018 | Hewitt | A61F 5/443 |
| 2020/0078206 A1* | 3/2020 | Chiladakis | A61F 5/449 |
| 2020/0297524 A1* | 9/2020 | Hunt | A61F 5/448 |
| 2022/0370233 A1* | 11/2022 | Lawton | A61F 5/449 |

OTHER PUBLICATIONS

International Search Report and Written Opinion for corresponding Application No. PCT/EP2019/064295 (mailed Jun. 19, 2020).

* cited by examiner

OSTOMY ATTACHMENTS

This application is a national stage application under 35 U.S.C. § 371 of International Application No. PCT/EP2019/064295, filed Jun. 3, 2019, which claims priority benefit of Great Britain Application No. 1809053.0, filed Jun. 1, 2018, which are hereby incorporated by reference in their entirety.

FIELD

The invention relates to the field of ostomy attachments.

BACKGROUND OF THE INVENTION

An ostomy is a surgically-created opening in the body to allow for discharge of bodily fluids, typically waste products. An ostomy is associated with a stoma, an externalising of a body cavity such as the intestine, ileum or ureter; the ostomy providing an alternative fluid outlet for that cavity via the stoma. Use of an ostomy typically follows surgery or disease that has disrupted the normal path of bodily fluids or waste through and/or from that body cavity.

The most common types of ostomy are: a colostomy, where the colon is diverted to an ostomy in the abdominal wall, typically following surgery to remove a lower part of the colon; ileostomy where a similar procedure is applied to the small intestine (the ileum); and a urostomy, where urine is drained through an ostomy where normal drainage through the bladder and ureter/urethra is not possible.

The stoma may present flush with the surface of the body at the ostomy or may protrude through the ostomy. Typically a bag or other suitable receptacle is attached to the patient's skin on an exterior face of the ostomy to collect bodily fluid as it is discharged from the stoma.

It is well documented that the bodily fluids discharged through a stoma can cause significant irritation if they come into contact with the skin surface surrounding the ostomy. It is therefore desirable to seal the connection between the ostomy and an ostomy bag that collects the waste in order to prevent the output from the stoma contacting the skin. However, the fact that each stoma is individually sized and shaped, along with the need to replace the bag and hence break the seal regularly, makes an optimum seal difficult to achieve in practice.

One known method of protecting the skin around a stoma from the stoma output is to make use of an ostomy seal. Typically formed of a biocompatible adhesive material such as hydrocolloid, an ostomy seal closely surrounds the ostomy, adhering to the skin on one side and a corresponding hydrocolloid seal around the entrance to an ostomy bag on the other.

Hydrocolloid, while providing excellent adherence and skin compatibility, can be an unstable material, and begins to lose it structural integrity once it starts to absorb water or other fluids. This can be through contact with the stomal output, for example. Loss of structural integrity of the hydrocolloid seal can result in uncontrolled expansion and warping of the material and/or breakdown of the hydrocolloid structure. Disruption of the hydrocolloid structure can lead to leakage from the seal or in some cases loss of adherence resulting in the ostomy bag detaching or falling off, which would be unhygienic and lead to odour and fluid loss which could be embarrassing for the patient.

Furthermore, the hydrocolloid on the ostomy bag and the hydrocolloid on the seal stick together easily and strongly on contact. This can cause the patient to struggle to accurately position the ostomy bag over the ostomy seal prior to the hydrocolloid layers sticking. The patient therefore has one chance to position the bag correctly, as once the hydrocolloid materials fuse it is very difficult to separate them again if re-positioning is needed. If the ostomy bag is not positioned accurately over the ostomy seal and around the patient's stoma, leaks and lack of adherence can result and as a consequence, if the bag is not positioned correctly first time, it may have to be disposed of, along with the seal, resulting in a wasted bag and seal. This results in unnecessary costs for the patient and/or medical provider.

Preventing waste of hydrocolloid material is of particular note as hydrocolloid material is expensive to produce. Hydrocolloid is typically manufactured in sheets or rolls. Circles of hydrocolloid are then cut from rolls or sheets and sold as ostomy seals, to protect the skin around the stoma. A hole is also cut out from the centre of the circular seal leading to a significant proportion of wasted hydrocolloid in a typical sheet. As hydrocolloid material is expensive it would be desirable to keep waste to a minimum.

EP0197672 describes a urostomy appliance that has a two-part form; a first part comprising a hydrocolloid adhesive pad that surrounds the stoma and a domed receptacle that is positioned over the stoma forming a seal with the hydrocolloid adhesive pad. The domed receptacle has a spout that has an entrance spaced from the skin for attachment to an ostomy bag. The spacing of the spout away from the skin does not direct the output from the stoma to the ostomy bag and allows pooling of stomal output on the hydrocolloid pad leading the instability issues and skin irritation outlined above.

WO 2017/167582 describes an ostomy attachment that addresses some of the above problems. A non-absorbent spout is attached to the hydrocolloid seal to effectively direct the output from the stoma to the ostomy bag. This helps avoid the absorbent seal material coming into contact with the ostomy output and reduces degradation in the way described above.

Nevertheless, assembling a flexible component made of a non-absorbent materials to a seal made of absorbent material, such as hydrocolloid, remains a challenge because of the hydrocolloid material's propensity to lose its structural integrity as it begins to absorb fluid from the effluent of a stoma. If the hydrocolloid loses its structural integrity, there may be a risk of the flexible, non-absorbent component separating from the hydrocolloid. Securing a non-absorbent component to hydrocolloid is possible by adhesive, heat seal, or other welding methods. While these methods would enable a bond between the two materials initially, they do not provide good adhesion during use when the hydrocolloid material may become unstable.

There remains a need in the art therefore for an ostomy attachment that effectively directs output from a stoma to an ostomy bag, preventing or minimising contact of the stomal output with the skin or the absorbent seal that is able to more securely attach and assemble a flexible non-absorbent component to a hydrocolloid ostomy seal. It is also desirable for the device to be easy for the patient to use and position. It is also desirable for the seal to be more economical to produce and prevent waste through improved manufacturing techniques.

These and other uses, features and advantages of the invention should be apparent to those skilled in the art from the teachings provided herein.

SUMMARY OF THE INVENTION

In a first aspect, the invention relates to an ostomy attachment comprising: a flexible annular seal configured to at least partially surround a stoma, the flexible annular seal having a first face and a second face; wherein the first face and the second face are each bounded by an inner rim and an outer rim, wherein the inner rim is concentrically arranged within the outer rim; and an ostomy seal liner configured to engage with the inner rim of the flexible annular seal; wherein the ostomy seal liner comprises one or more stabilising extensions, wherein the one or more stabilising extensions extend from the ostomy seal liner radially outward and over the first face of the flexible annular seal; and wherein the one or more stabilising extensions are in contacting relation with the first face of the flexible annular seal. In an embodiment, the one or more stabilising extensions are in substantially continuous contacting relation with the first face of the annular seal.

In embodiments, the one or more stabilising extensions extend across the first face of the flexible annular seal by at least 30% of the distance between the inner rim and the outer rim. In further embodiments, the stabilising extensions are substantially planar. In other embodiments, the or each stabilising extension comprises one or more apertures or relief areas.

In embodiments, the annular seal is formed of absorbent material and the ostomy seal liner is formed of non-absorbent material. Suitably, the absorbent material is a hydrocolloid.

In embodiments, the ostomy seal liner comprises at least one resiliently deformable arm. Suitably, the or each stabilising extension is positioned at the end of the or each resiliently deformable arm. More suitably, the ostomy seal liner comprises two resiliently deformable arms. In embodiments, the ostomy seal liner further comprises a central section to which the at least one resiliently deformable arm is attached. In embodiments, the central section comprises a spout that in use is disposed beneath the stoma and/or is configured to direct ostomy output away from a patient's skin and into an ostomy bag. Suitably, the spout is angled to optimise collection of ostomy output and delivery of ostomy output into an ostomy bag. Suitably, the resiliently deformable arm is attached at both ends to the central section to form an annular ring.

In embodiments, the one or more stabilising extensions are positioned substantially regularly spaced around a circumference of the annular ring. In other embodiments, the one or more stabilising extensions extend outwardly from no more than 30% of the length of the at least one resiliently deformable arm. In embodiments, the ostomy seal liner is fixedly attached to the annular seal.

In a second aspect the invention relates to an ostomy attachment kit comprising the ostomy attachment of the first aspect of the invention and an ostomy bag. Suitably, the ostomy bag comprises an ostomy bag seal for attachment to the annular seal of the ostomy attachment.

In a third aspect, the invention relates to a method for attaching an ostomy bag to a patient with a stoma, comprising the steps of: placing the ostomy attachment of the first aspect of the invention on the patient such that the flexible annular seal at least partially surrounds the patient's stoma; and attaching an ostomy bag to the annular seal of the ostomy attachment.

In a fourth aspect, the invention relates to an ostomy attachment comprising: a flexible annular seal configured to surround the periphery of a stoma; and an ostomy seal liner configured to engage with an inner rim of the annular seal; wherein the ostomy seal liner comprises a spout section and a lateral protrusion, the lateral protrusion being located between the spout section and the annular seal and extending generally parallel to and at least partially over a face of the annular seal, wherein the lateral protrusion is configured for engagement with a corresponding ostomy bag seal prior to contact of the annular seal with the ostomy bag seal. Suitably, the lateral protrusion is located under the angled spout of the spout section and over a face of the annular seal and extending generally parallel to and at least partially over the face of the annular seal.

In embodiments, in use, the spout section is disposed or configured to be beneath the stoma and is configured to collect, or collects, ostomy output at skin level and direct ostomy output away from the skin and into an ostomy bag. In embodiments the spout section is angled radially outwardly from the inner rim of the annular seal and away from the at least one face of the annular seal. In other embodiments the annular seal is formed of absorbent material and the ostomy seal liner is formed of non-absorbent material. Suitably, the absorbent material is a hydrocolloid. In embodiments, the ostomy seal liner is detachably attached to the annular seal.

In a fifth aspect, the invention relates to a method for attaching an ostomy bag to a patient with a stoma, comprising the sequentially ordered steps of: placing the ostomy attachment of the third aspect of the invention on a patient such that the flexible annular seal at least partially surrounds the patient's stoma; offering up an ostomy bag to the ostomy attachment such that a seal of the ostomy bag contacts the lateral protrusion and does not contact the annular seal; aligning the seal of the ostomy bag with the annular seal of the ostomy attachment; and attaching the ostomy bag to the ostomy attachment. In this context, "sequentially ordered" means the steps are performed in the order as written, optionally with other steps interspaced between one or more steps. Suitably, "sequentially ordered" means the steps are performed in the order as written, with no other non-trivial steps interspaced between one or more steps.

In a sixth aspect, the invention relates to an ostomy seal liner for use in the ostomy attachments of any one of the first and/or third aspects of the invention. The ostomy seal liner of this aspect may have any one of the features described of the ostomy seal liner in embodiments of the ostomy seal attachment of the first aspect of the invention or otherwise described herein.

In a seventh aspect, the invention relates to an annular hydrocolloid ostomy seal for at least partially surrounding a stoma formed of at least two pieces. Suitably, the seal is formed of two pieces.

In an embodiment, each of the pieces of the seal has a semi-circular shape.

In an eighth aspect, the invention relates to a semi-circular piece of an ostomy seal according to the seventh aspect of the invention.

BRIEF DESCRIPTION OF THE DRAWINGS

One or more embodiments of the invention will now be described, by way of example only, with reference to the accompanying drawings, in which.

DETAILED DESCRIPTION OF THE INVENTION

Figure 1:
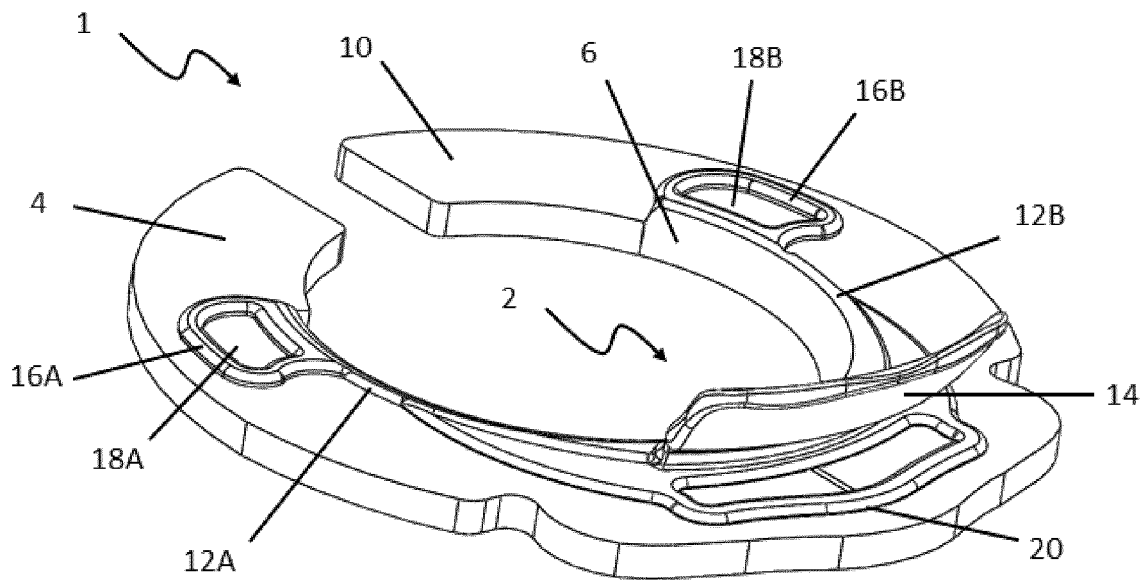
FIGS. 1 and 2 are representations of an embodiment of an ostomy attachment according to the invention.

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

Unless otherwise indicated by context, the use herein of the singular is to be read to include the plural and vice versa. As such the terms "a", "an", "one or more" and "at least one" are used interchangeably herein.

As used herein, the term 'comprising' means any of the recited elements are necessarily included and other elements may optionally be included as well. 'Consisting essentially of' means any recited elements are necessarily included, elements which would materially affect the basic and novel characteristics of the listed elements are excluded, and other elements may optionally be included. 'Consisting of' means that all elements other than those listed are excluded. Embodiments defined by each of these terms are within the scope of this invention.

As used herein the term "absorbent" refers to a property of a material in which it can absorb water or other liquids. The term "absorbent material" refers to a material that has absorbent properties. The absorbent material may be materially affected by absorbing the water or other liquids, for example, the material may expand, distort, become unstable, degenerate or decompose. Examples of absorbent materials in the context of the present application are hydrocolloids and hydrogels. In contrast, the term "non-absorbent" refers to a property of a material in that it does not absorb water or other liquids. The term "non-absorbent material" refers to a material that has non-absorbent properties. The non-absorbent material may remain visibly and structurally unchanged after contact with these liquids. Examples of non-absorbent materials in the context of the present application are rubber, rubber-like materials, polyurethanes, silicones and thermoplastic elastomers. Further examples of non-absorbent materials may be thermosetting plastics and metals, such as shape-memory metals or foils.

As used herein the term "hydrocolloid" refers to a material that typically contain polymers such as polyisobutylene, and hydroactive particles such as sodium carboxymethyl cellulose, gelatine and pectin. The hydrocolloid swells on contact with hydrophilic fluids to form a semi-solid gel.

As used herein the term "resiliently deformable" refers to the ability of a material or a structure to bend or flex under a suitable force and when that force is removed to return substantially or exactly to the original shape or position.

As used herein the term "flexible" refers to the ability of a material or a structure to bend or flex under a suitable force.

As used herein the term "ostomy seal" or "seal" refers to a component that forms part of an ostomy attachment or ostomy bag and acts to provide a fluid-tight seal between the stoma and the ostomy bag in which stomal output collects. Typically, an ostomy seal is biocompatible and is safe to use in contact with skin. Suitably, the ostomy seal has adhesive properties meaning it may adhere to the skin and/or other parts of the ostomy attachment or bag. Suitably the ostomy seal is formed of an absorbent material such as hydrocolloid or a hydrogel. In embodiments, the ostomy seal is a planar annular ring (complete or broken one or more times by radial cuts) having an inner face and an outer face, wherein the outer face us generally perpendicular to the inner face, An inner wall or inner rim, generally perpendicular to the inner and outer face borders and/or surrounds a central opening in the ostomy seal. Concentrically arranged outside of, and generally parallel to the inner rim, is an outer wall or outer rim. Typically, ostomy seal is planar having a distance between the inner and the outer face that is less than the distance between diametrically opposed points on the outer rim.

As used herein the term "ostomy seal liner" refers to a component that forms part of an ostomy attachment and at least partially contacts an ostomy seal. The ostomy seal liner may, sit at least partially within the inner rim of a generally annular, or partially annular ostomy seal and optionally partially on the surface of one or more faces of an ostomy seal. An ostomy seal liner may act to provide a physical barrier that minimises or prevents contact of stomal output with an ostomy seal.

As used herein the term "stabilising extension" refers to a component or appendage of an ostomy seal liner that on assembly of the ostomy attachment, or ostomy attachment and ostomy bag, provides additional mechanical fixation of the ostomy seal to the ostomy seal liner. A stabilising extension may be plate-like, or planar. A stabilising extension may have geometric shape or an irregular shape that extends outwardly from an ostomy seal liner over and/or into an ostomy seal. In embodiments, the or each stabilising extension on an ostomy seal liner are discrete units that are spaced apart from each other around a circumference (or approximation thereto) on an ostomy seal liner. The stabilising extension may be configured to be in at least partial contact with the ostomy seal. On assembly of the ostomy attachment, or ostomy attachment with an ostomy bag, the stabilising extension may become positioned or sandwiched between, or embedded within, an ostomy seal and/or another component, such as a further ostomy seal on the ostomy bag, such that there is provided an increased physical impediment to the separation of the ostomy seal liner and the ostomy seal, particularly when in use. The stabilising extension may be solid, or may comprise one or more relief areas (or indents), or holes or apertures such that the material of the ostomy seal may extend thereinto, or in embodiments fuse therethrough, to provide an enhanced mechanical fixation.

The present invention provides an improved ostomy attachment that more securely assembles an ostomy seal liner with an ostomy seal to improve the stability and longevity of the ostomy attachment in use. The present invention also provides for an improved ostomy attachment that is easier for the patient to use and position. The present invention also provides for an improved ostomy seal that is more economical to produce and prevents waste through improved manufacturing techniques.

Figure 2:
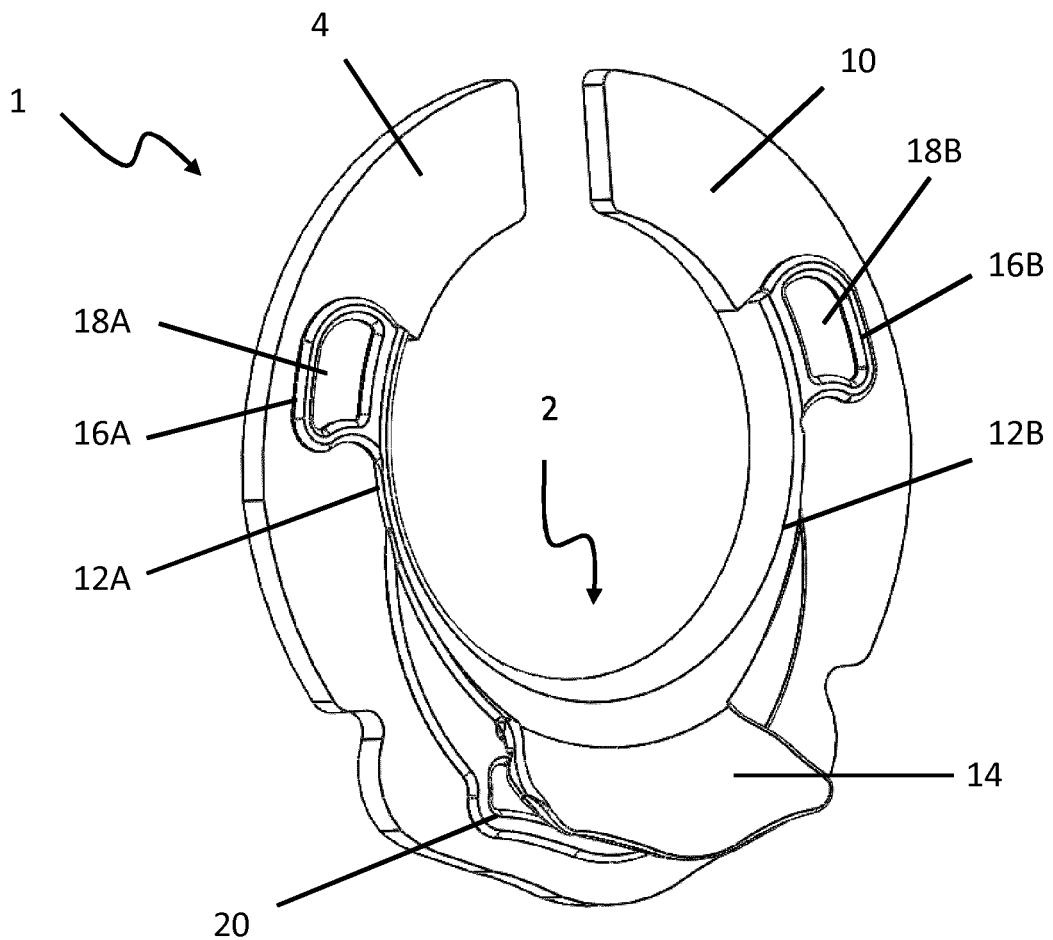

FIGS. 1 and 2 of the drawings show an ostomy attachment 1 according to one embodiment of the invention. The ostomy attachment 1 shown comprises an annular seal 4 and an ostomy seal liner 2.

In an embodiment, the annular seal 4 is in the form of a planar, substantially annular, ring having an outer rim with a corresponding outer circumference and an inner rim 6 with a corresponding inner circumference. Suitably, the inner circumference is dimensioned such that, in use, the annular seal 4 can be manipulated to closely surround a patient's stoma.

Figure 5:
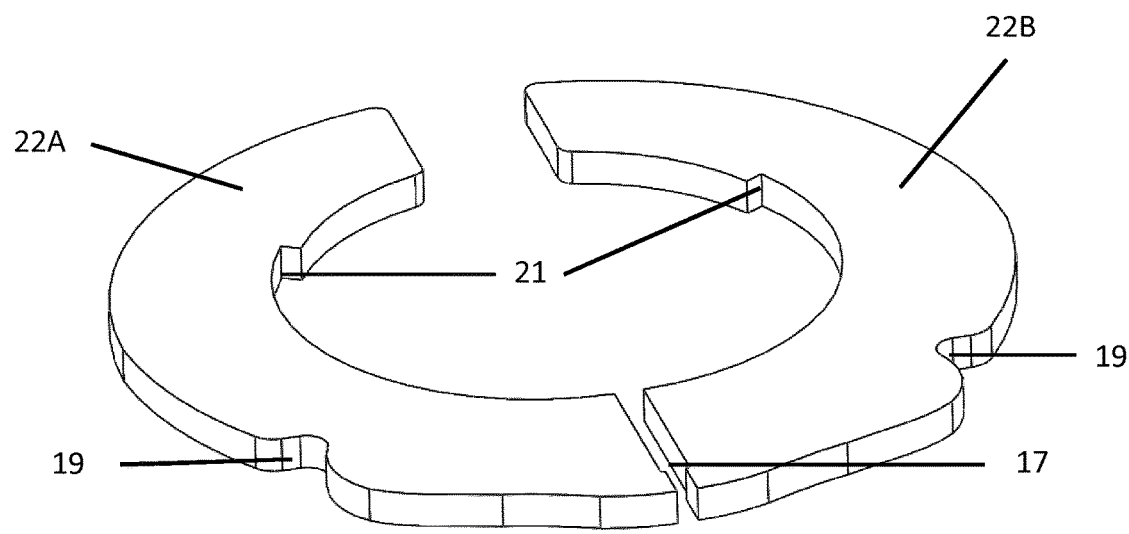
FIG. 5 is a representation of two semi-circular halves of an ostomy seal in accordance with an embodiment of the invention.

In the prior art, the annular seal 4 is commonly a complete annular ring. In the embodiment shown in FIGS. 1 and 2, the annular seal 4 is broken at one position i.e. the annular seal is a partially annular seal. Such an arrangement can assist in adapting the inner circumference of the ostomy seal 4 to obtain an optimised fit around the stoma. An annular seal 4 without a break, or with more than one break, for example, a seal with two breaks generally diametrically opposed to each other, as best shown in FIG. 5, would also be suitable for use in the invention. The ostomy seal may have three, four or more breaks and therefore be present as one, two, three, four, or five or more pieces.

In embodiments, the annular seal 4 may have adaptations 19 to enhance flexibility to assist in adapting the annular seal to the shape of the patient's stoma. The adaptations may be one or more cuts or incisions that extend radially across the annular seal but do not extend fully across the seal so as not to separate the seal at that position. Alternatively, or in addition, the adaptations may comprise shaping of the contours of the outer or inner rim resulting in variation of the planar width of the seal at one or more given points.

The dimensions of the annular seal 4 may be adapted to the particular stoma for which use is intended. Alternatively, the inner circumference of the annular seal is chosen to be of one dimension, and the flexibility of the annular seal 4 is used to adapt to a given stoma size by manipulation, cutting, and/or snapping, breaking or a combination thereof. The annular seal 4 may be generally circular, although any suitable shape is contemplated. In all cases, the internal diameter of the opening in the annular seal may be defined as the minimum distance between two edges of the inner rim of the annular seal when measured through a geometric centre, or approximation thereto, in a central opening in the annular seal 4, as manufactured, i.e. in its pre-use state. Suitably, the inner diameter of annular seal 4 may be 1.0 cm or less, 1.5 cm, 2.0 cm, 2.5 cm, 3.0 cm, 3.5 cm, 4.0 cm, 4.5 cm, 5.0 cm, 5.5 cm, 6.0 cm, 6.5 cm, 7.0 cm, 7.5 cm, 8.0 cm, 8.5 cm, 9.0 cm, 10.0 cm or more. The external diameter of the annular seal may be defined as the minimum distance between two edges of the outer circumference of the annular seal when measured through a geometric centre or an approximation thereto, in the opening in the annular seal 4, as manufactured, i.e. in its pre-use state. Suitably, the outer diameter of annular seal 4 may be 2.0 cm or less, 2.5 cm, 3.0 cm, 3.5 cm, 4.0 cm, 4.5 cm, 5.0 cm, 5.5 cm, 6.0 cm, 6.5 cm, 7.0 cm, 7.5 cm, 8.0 cm, 8.5 cm, 9.0 cm, 10.0 cm, 10.5 cm, 11.0 cm, 11.5 cm, 12.0 cm, 12.5 cm, 13.0 cm, 13.5 cm, 14.0 cm, 14.5 cm, 15.0 cm or more.

In an embodiment, an inner surface or face of the annular seal 4 abuts and adheres to the skin and the outer face 10, substantially parallel to and opposite the inner face, provides an attachment site for an ostomy bag (not shown) via an ostomy bag seal (not shown) on the ostomy bag. The inner and outer circumference may be selected such that sufficient surface area is provided on the annular seal 4 to result in good adherence of the outer face 10 of the annular seal 4 with the ostomy bag seal.

In embodiments, the surface area of one face of the annular seal may be between 1 $cm^2$ and 50 $cm^2$, suitably 3 $cm^2$ and 30 $cm^2$, more suitably 3 $cm^2$ and 10 $cm^2$. Suitably, the minimum surface area of one face of the annular seal may be 1 $cm^2$, 2 $cm^2$, 3 $cm^2$, 4 $cm^2$, 5 $cm^2$, 6 $cm^2$, 7 $cm^2$, 8 $cm^2$, 9 $cm^2$, 10 $cm^2$, 11 $cm^2$, 12 $cm^2$, 13 $cm^2$, 14 $cm^2$, 15 $cm^2$, 16 $cm^2$, 17 $cm^2$, 18 $cm^2$, 19 $cm^2$, 20 $cm^2$, or more. Suitably, the maximum surface area of one face of the annular seal may be 50 $cm^2$, 40 $cm^2$, 30 $cm^2$, 25 $cm^2$, 20 $cm^2$, 19 $cm^2$, 18 $cm^2$, 17 $cm^2$, 16 $cm^2$, 15 $cm^2$, 14 $cm^2$, 13 $cm^2$, 12 $cm^2$, 11 $cm^2$, 10 $cm^2$, or less.

The thickness of the annular seal 4, measured as the distance between the inner face and the outer face may be any suitable dimension that maintains the structural integrity of the seal and the ostomy attachment to which is applied in use. Suitably, the thickness of the annular seal may be minimised to reduce the amount of material, such as hydrocolloid, used in the seal. Suitably, the thickness of the annular seal is at least 0.1 mm, 0.5 mm, 1 mm, 2 mm, 3 mm, 4 mm, 5 mm, 6 mm, 7 mm, 8 mm, 9 mm, 10 mm or more. Suitably, the thickness of the annular seal is at most 10 mm, 9 mm, 8 mm, 7 mm, 6 mm, 5 mm, 4 mm, 3 mm, 2 mm, 1 mm, or less In embodiments, and in the embodiment shown in FIGS. 1 and 2, the ostomy seal liner 2 comprises two resiliently deformable arms 12A, 12B each extending from a central section 14. In other embodiments, a single arm may be used, or the arm may be fixed to the central section 14 at both ends to form an annular ring. In an embodiment, the arms 12A, 12B are curved such that the ostomy seal liner 2 has a at least part-annular appearance in plan view, and dimensioned such that the outer edge of one or more of arms or the central portion of the ostomy seal liner 2 may conform closely with the inner rim 6 of the annular seal 4. In embodiments, the annular seal 4 and/or the ostomy seal liner 2 may be adapted to have corresponding features 21 to enhance the conformity of the fitment. For example, and as best shown in FIG. 5, the annular seal may have radial cut-outs in the inner rim 6 to accommodate the resiliently deformable arms 12A, 12B and central section 14. Such adaptations further enhance the structural integrity of the assembly of the two components.

In use, the ostomy seal liner 2 acts to shield the annular seal 4 from the ostomy fluid leaving the stoma or held in the ostomy bag to which the ostomy attachment is attached. In an embodiment, the ostomy seal liner 2 closely conforms to the annular seal 4 at least under or below the stoma, suitably in partial or full circumference, when in use. Under the force of gravity fluid leaving the stoma will pass downward and be directed by the ostomy seal liner 2 to the ostomy bag and thereby prevent or reduce the propensity of the fluid contacting the patient's skin and/or the annular seal 4.

The central section 14 is configured to collect and direct ostomy output away from the annular seal 4 and the patient's skin. The central section 14 of the ostomy seal liner 2 may be provided to or closely approaching skin level to improve or optimise collection of ostomy output and prevent or reduce the amount of stomal fluid contacting the skin and/or the annular seal 4. In embodiments, such as the embodiment shown in FIGS. 1 and 2, the central section 14 forms a spout-like feature that is angled with respect to a face of the annular seal 4, projecting downwardly and outwardly, away from the centre of the annular seal 4, or the stoma in use. In other words, the central section 14 is configured to project away from the intended face of attachment to the patient, extending radially and longitudinally outwardly with respect to a longitudinal axis that passes through the centre point (or an approximation thereto) of the annular seal 4. In this way, ostomy output is directed away from the skin and/or the annular seal 4 and into the ostomy bag.

The spout in accordance with the invention may be any suitable shape and size. Suitably, the spout is generally quadrangular in shape. In embodiments, the spout is between 1 cm and 5 cm long. Suitably, the spout is between 1 cm and 3 cm long. In embodiments, the spout has a maximum length of 0.5 cm or less, 1 cm, 1.5 cm, 2 cm, 2.5 cm. 3 cm, 3.5 cm, 4.0 cm or more. In embodiments, the spout has a maximum length of 7.0 cm or more, 6.5 cm, 6.0 cm, 5.5 cm, 5.0 cm or less. In further embodiments, the spout is between 1 cm and 5 cm wide. Suitably, the spout is between 1 cm and 3 cm wide. the spout has a minimum width of 0.5 cm or less, 1 cm, 1.5 cm, 2 cm, 2.5 cm. 3 cm, 3.5 cm, 4.0 cm or more. In embodiments, the spout has a maximum width of 7.0 cm or more, 6.5 cm, 6.0 cm, 5.5 cm, 5.0 cm or less.

Due to the angle of the spout in certain embodiments, the height of the spout (defined as the perpendicular distance between the end of the spout furthest from the annular seal 4 and the first face of the annular seal 4 (or extended plane thereof) is between 1 cm and 5 cm. Suitably, the height of the spout is between 1 cm and 3 cm long. In embodiments, the minimum height of the spout is 0.5 cm or less, 1 cm, 1.5 cm, 2 cm, 2.5 cm. 3 cm, 3.5 cm, 4.0 cm or more. In embodiments, the maximum height of the spout is 7.0 cm or more, 6.5 cm, 6.0 cm, 5.5 cm, 5.0 cm or less.

The central section 14, particularly in embodiments where this is in the form of a spout, may also provide an overhang which acts to obstruct or prevent ostomy output in the bag splashing back against the annular seal 4, and in use the stoma and the surrounding skin area.

In embodiments, the central section 14 of the ostomy seal liner 2 also act to prevent the front face of the ostomy bag contacting or closing onto the stoma or opening 6 in the annular seal such that it impedes or blocks of the flow of stomal fluid into the ostomy bag, so-called "pancaking" or "pattycaking". This can otherwise lead to leaks and/or increase contact of the stomal fluid on the skin and/or the annular seal 4.

In embodiments, the ostomy seal liner 2 has additional or alternative features that fix or otherwise integrate the ostomy seal liner 2 with the ostomy seal 4. In embodiments, the ostomy seal liner 2 may have one or more extensions 15 that project substantially perpendicular to the plane in which the one or more arms 12A, 12B extend and/or the plane of the annular seal 4. The extension 15 may be configured to extend into a corresponding cut or indentation in an ostomy seal 4 when the ostomy attachment 1 is assembled. In the embodiment of the ostomy seal liner 2 shown in FIG. 3, the extension 15 takes the form of an upstanding wall that, as best seen in FIG. 1, may lie within a partial or full cut of the ostomy seal 17. In embodiments, the extension 15 sits within the ostomy seal 4 and does not extend beyond or outside of the opposing face of the ostomy seal 4. In embodiments, the extension 15 has a relief or indent such that the neighbouring areas of the ostomy seal 4 may fuse through the relief area, or extend into the indent, to provide or enhance the security of the fixing of the extension in the ostomy seal 4.

The ostomy seal liner 2 may be formed of any suitable material. Suitably, the ostomy seal liner 2 is formed of a non-absorbent material that is resistant to deformation and/or degradation from contact with output from the stoma. Suitably, the ostomy seal liner 2 is resiliently deformable or flexible such that it can be manipulated to conform to the shape of the annular seal 4. Any material with the required properties would be suitable to form the ostomy seal liner 2; specific examples include rubber, rubber-like materials, polyurethanes, silicones and thermoplastic elastomers. In embodiments, the annular seal 4 is formed of a flexible, absorbent material that provides biocompatibility and adherence such as hydrocolloid, hydrogels and other absorbent materials that may have applications in the wound care and ostomy industry. Suitably, the material is a hydrocolloid. Other materials may be used in combination with a suitable biocompatible adhesive.

The ostomy seal liner 2 is configured to couple or attach or fix to the annular seal 4. The means of fixing may be: permanent, for example via plastic welding; semi-permanent, for example by adhesion, or fusion of the annular seal 4 through or into parts of the ostomy seal liner; or reversible, for example via friction, semi-permanent adhesion, or biased resilient attachment points; or a combination of these. In embodiments, such as the embodiment shown in FIG. 1, the ostomy seal liner 2 is positioned within the inner rim 6 of the annular seal 4 and held in place by the biasing force of the resiliently deformable arms 12A, 12B pressing outwardly against the annular seal 4, and/or the through the annular seal 4 adhering to the ostomy seal liner 2 at points where the annular seal 4 and the seal liner 2 come into contact. Additional attachment or fixing may be realised in embodiments, such as the embodiment shown in FIGS. 1 and 2 by the extension 15 projecting into, and being secured within, the ostomy seal 4.

The ostomy attachment 1 may be provided to the patient pre-assembled with the ostomy seal 4 already attached to the ostomy seal liner 2, or the components of the ostomy attachment 1 may be provided separately for the user to assemble prior to use.

In use, the attachment 1 is positioned against a user's skin at least partially embracing or surrounding the circumference of a user's stoma oriented such that the central section 14 is disposed substantially beneath the stoma. The annular seal 4 is then adjusted such that it optimally conforms to the periphery of the stoma, forming a good seal between the ostomy attachment and the stoma. In embodiments, the resiliently deformable arms 12A, 12B follow the contours of the annular seal 4 as it is manipulated into position. An ostomy bag is then attached to the attachment 1. A fluid-tight bond is formed between the annular seal 4 and the corresponding seal on the ostomy bag. When the material of the respective seals is hydrocolloid the seal is formed by the fusing of the hydrocolloid material present in the annular seal 4 and the seal on the ostomy bag. This also creates a secure attachment. Other forms of attachment using adhesive, plastic welding or physical means such as clips or fixings are also contemplated.

Figure 3:
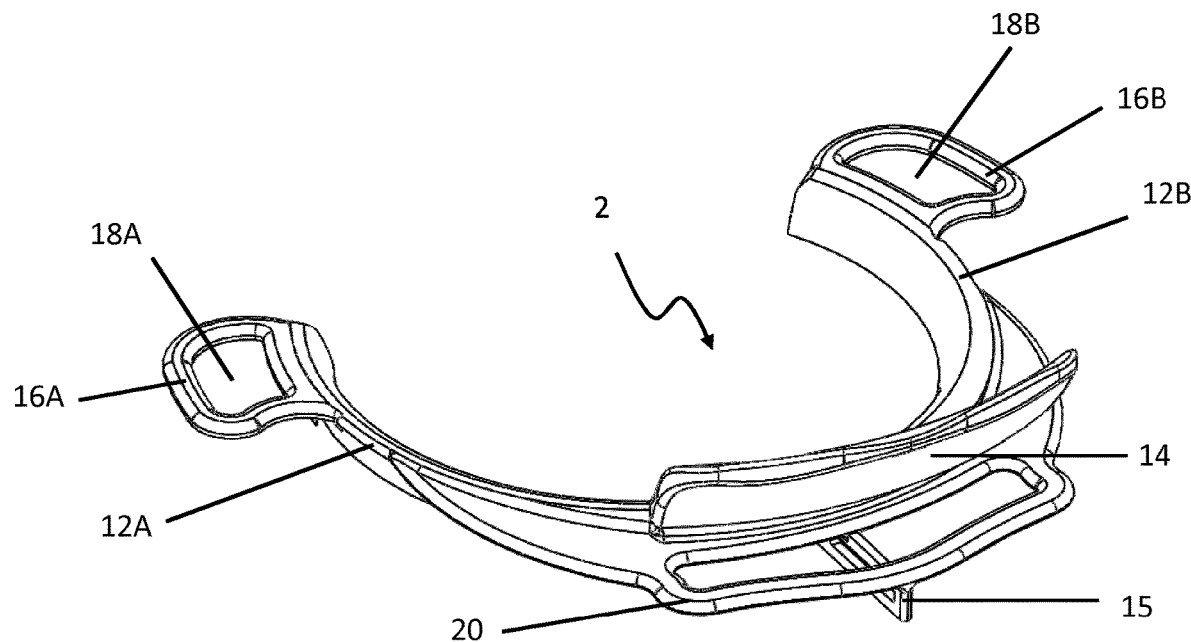
FIG. 3 is a representation of an embodiment of an ostomy seal liner according to the invention.
Figure 4:
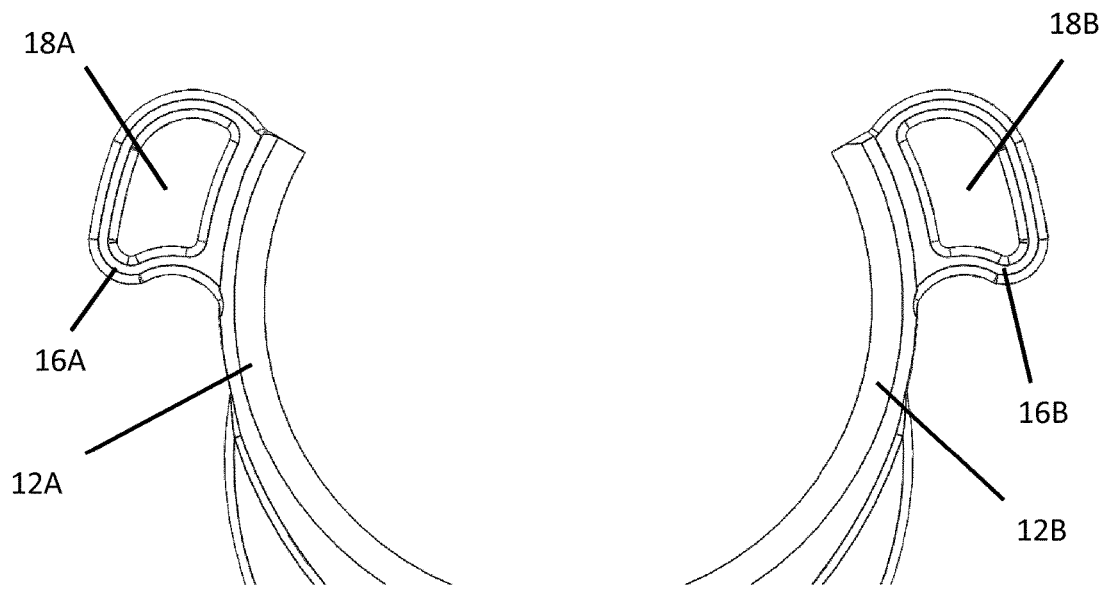
FIG. 4 is a representation of stabilising extensions on an embodiment of an ostomy seal liner according to the invention.

In embodiments of the present invention and as best seen in FIGS. 3 and 4, at least one of the resiliently flexible arms 12A, 12B on the ostomy seal liner 2 comprises a stabilising extension 16A, 16B. Suitably the or each resiliently deformable arm 12A, 12B comprises a stabilising extension 16A, 16B. The stabilising extensions 16A, 16B may be positioned anywhere on the arms 12A, 12B. In embodiments where the resiliently deformable arms 12A, 12B have a free end, the stabilising extensions are positioned at or towards the free end of the resiliently deformable arms 12A, 12B. In embodiments where the resiliently deformable arm 12A, 12B is joined at both ends to a central section 14, the stabilising extensions may be positioned in suitable spaced relation around the circumference of the ostomy seal liner 2.

The stabilising extensions 16A, 16B may be any suitable shape and size. Suitably, the stabilising extensions 16A, 16B are plate-like, i.e. planar. Suitably, the stabilising extensions 16A, 16B have a geometric shape, suitably the geometric shape has an edge distal from the ostomy seal liner 2 that is either the same, lesser or greater length than the edge attached to the ostomy seal liner 2. Suitably, the extensions 16A, 16B extend from the inner rim 6 of the annular seal 4 across the outer face of the annular seal 4. The stabilising extension 16A, 16B may extend substantially all the way across the outer face of the annular seal 4. Suitably, a stabilising extension 16A, 16B extends part way across the outer face of the annular seal 4. More suitably, the extensions 16A, 16B extend more than half way across the face of the annular seal 4 from the inner rim 6 to the outer rim of the annular seal 4. Suitably, the stabilising extension 16A, 16B do not extend beyond the outer rim of the seal 4. Suitably, the stabilising extension 16A, 16B extend 10%, 20%, 30%, 40%, 50%, 60%, 70%, 80%, 90%, 100% across the annular seal 4. In an embodiment, at least part of the stabilising extensions 16A, 16B is configured to be in contact with the outer face of the annular seal 4. Suitably, substantially all of the stabilising extension 16A, 16B is configured to be in contact with the outer face of the annular seal 4.

In embodiments, the stabilising extension 16A, 16B extends outwardly from the ostomy seal liner 2 for no more than 5% of the combined total length of the one or more resiliently deformable arms 12A, 12B and the central section 14 (when present). Suitably, the stabilising extension 16A, 16B extends outwardly from the ostomy seal liner 2 for no more than 10%, 15%, 20%, 25%, 30%, 35%, 40%, 45%, 50% or more of the total length of the one or more resiliently deformable arms 12A, 12B and the central section 14 (when present). Suitably the total of all stabilising extensions 16A, 16B extends outwardly from the ostomy seal liner 2 for no more than 10%, 15%, 20%, 25%, 30%, 35%, 40%, 45%, 50% or more of the total length of the one or more resiliently deformable arms 12A, 12B and the central section 14 (when present). Suitably the total arcuate circumference of all stabilising extensions 16A, 16B extending outwardly from the ostomy seal liner 2 for no more than 10° or less, 15°, 20°, 25°, 30°, 35°, 40°, 45°, 50° or more as measured at the join of the stabilising extensions 16A, 16B to the ostomy seal liner, or at the radially outer edge of the stabilising extensions 16A, 16B, or at a widest mid-point of the stabilising extensions 16A, 16B.

In embodiments, the total area of the or each stabilising extensions 16A, 16B (including any relief area or hole or aperture area within the stabilising extension 16A, 16B) is between 0.5 cm² to 2 cm². Suitably, the total area of the or each stabilising extensions 16A, 16B (including any relief area or hole or aperture area within the stabilising extension 16A, 16B) is between 1.0 cm² to 1.5 cm². Suitably, the total area of the or each stabilising extensions 16A, 16B (including any relief area or hole or aperture area within the stabilising extension 16A, 16B) is at least 0.1 cm², 0.2 cm², 0.3 cm², 0.4 cm², 0.5 cm², 0.6 cm², 0.7 cm², 0.8 cm², 0.9 cm², 1.0 cm², 1.1 cm², 1.2 cm², 1.3 cm², 1.4 cm², 1.5 cm², 1.6 cm², 1.7 cm², 1.8 cm², 1.9 cm², 2.0 cm², 2.5 cm², 3.0 cm² or more. Suitably, the total area of the or each stabilising extensions 16A, 16B (including the surface area of any relief area or hole or aperture area within the stabilising extension 16A, 16B) is at most 5.0 cm², 4.5 cm², 4.0 cm², 3.5 cm², 3.0 cm², 2.5 cm², 2.0 cm² or less.

In embodiments, the total area total area of all stabilising extensions 16A, 16B (including any relief area or hole or aperture area within the stabilising extension 16A, 16B) is between 0.5 cm² to 10 cm². Suitably, the total area of all stabilising extensions 16A, 16B (including any relief area or hole or aperture area within the stabilising extension 16A, 16B) is between 2.0 cm² to 5.0 cm². Suitably, the total area of all stabilising extensions 16A, 16B (including any relief area or hole or aperture area within the stabilising extension 16A, 16B) is at least 0.1 cm², 0.2 cm², 0.3 cm², 0.4 cm², 0.5 cm², 0.6 cm², 0.7 cm², 0.8 cm², 0.9 cm², 1.0 cm², 1.1 cm², 1.2 cm², 1.3 cm², 1.4 cm², 1.5 cm², 1.6 cm², 1.7 cm², 1.8 cm², 1.9 cm², 2.0 cm², 2.5 cm², 3.0 cm², 3.5 cm², 4.0 cm², 4.5 cm², 5.0 cm², or more. Suitably, the total area of all stabilising extensions 16A, 16B (including any relief area or hole or aperture area within the stabilising extension 16A, 16B) is at most 10.0 cm², 9.5 cm², 9.0 cm², 8.5 cm², 8.0 cm², 7.5 cm², 7.0 cm², 6.5 cm², 6.0 cm², 5.5 cm², 5.0 cm², 4.5 cm², 4.0 cm², or less.

In embodiments, the stabilising extensions 16A, 16B increase the surface area of the ostomy seal liner 2 in contact with the annular seal 4 which aids adhesion and/or otherwise fixing of the ostomy seal liner 2 to the annular seal 4. particularly when, in use, the stabilising extension 16A, 16B are positioned between, i.e. "sandwiched" between the annular seal 4 and the corresponding seal or other component on an ostomy bag. Suitably, the stabilising extensions 16A, 16B lay flat between the annular seal 4 and the corresponding seal of the ostomy bag so as to minimally interfere with or reduce the contact area of these two seals.

In embodiments, the stabilising extension 16A, 16B may be solid. In embodiments the stabilising extension 16A, 16B are flat planar structures. In some embodiments, the stabilising extension 16A, 16B may have walls, undulations or other forms of markings or three-dimensional structure to increase lateral resistance to movement when positioned between or adjacent to seal material. Suitably, the stabilising extension 16A, 16B comprise a relief or detent, or one or more openings 18A, 18B (also referred to as apertures, loops, gaps or holes) in the extension 16A, 16B. The relief or opening in the stabilising extension 16A, 16B means that there is an area of seal material, suitably an absorbent material such as hydrocolloid, exposed through the opening, or under the relief in the stabilising extension 16A, 16B. In use, this area of material, along with the remaining material on the outer surface of the annular seal 4, will fuse with the corresponding material, suitably hydrocolloid, on the ostomy bag seal (not shown), once the ostomy bag is attached to the ostomy attachment 1. As the absorbent material in the annular seal 4 contacts a corresponding seal on an ostomy bag, or as it expands as it absorbs fluid from the output of the stoma, the piece of seal material will expand through the opening 18A, 18B, or into the relief, in the stabilising extension 16A, 16B of the ostomy seal liner 2, fusing with the absorbent material in the ostomy bag seal resulting in a mechanical fixation that retains the stabilising extension 16A, 16B in the unitary seal formed between the fusion of the annular seal 4 and ostomy bag seal. This provides an improved means of securing the ostomy seal liner 2 to the annular seal 4 when the attachment 1 is in use.

In all embodiments, the stabilising extensions 16A, 16B inherently decrease the contact surface area between the annular seal 4 and the seal on the ostomy bag at least to some extent. As in prior art devices the contact area is responsible for adhesion of the ostomy bag to any ostomy attachment, and provides the fluid tight seal, it would therefore not have been an obvious adaptation in view of the state of the art to position part of the ostomy attachment over or within the seal which may impede or reduce the contact area of the seal. Nevertheless, in the ostomy attachment 1 of the present invention which comprises an annular seal 4 and an ostomy seal liner 2, the stabilising extensions 16A, 16B assist in the structural integrity and longevity in use of the assembled attachment 1 in accordance with the present invention.

In a further aspect of the invention, and as best shown in FIG. 3, the ostomy seal liner 2 comprises a lateral protrusion 20. The lateral protrusion 20 may be positioned anywhere on the ostomy seal liner 2. In the embodiment shown, the lateral protrusion 20 is located under the central section 14. In embodiments, the lateral protrusion 20 is configured to extend outwardly from the centre or approximation thereto of the ostomy seal liner 2 and over the annular seal 4. The lateral protrusion 20 may be in substantially complete, or partial contacting relation with the outer face of the annular seal 4. The lateral protrusion 20 may extend substantially all the way across the outer face of the annular seal 4. Suitably, lateral protrusion 20 extends part way across the outer face of the annular seal 4. More suitably, the lateral protrusion 20 extends more than half way across the face of the annular seal 4 from the inner rim 6 to the outer rim of the annular seal 4. Suitably, the lateral protrusion 20 does not extend beyond the outer rim of the seal 4. Suitably, the lateral protrusion 20 extends 10%, 20%, 30%, 40%, 50%, 60%, 70%, 80%, 90%, 100% across the annular seal 4.

In an embodiment, the lateral protrusion 20 is unitary with and formed of the same material as the remainder of the ostomy seal liner 2 and is suitably non-absorbent and at least partially resiliently deformable or flexible.

The annular seal 4 and the corresponding seal on an ostomy bag (not shown) are intended to adhere to each other rapidly to form a strong bond. When the material of each seal is the absorbent material hydrocolloid, the material on each seal may fuse together to form a single unitary seal. While a quick and strong bond is useful to prevent leaks and for ease of use, it can result in misalignment of the ostomy bag on the annular seal 4 when it is offered up incorrectly. Misalignment may lead to leaks or lack of adherence of the bag. If the bag is misaligned, once bonded, the bag and the attachment typically need to be discarded and a new attachment and bag used leading to unnecessary waste.

The lateral protrusion 20 acts to cover or otherwise prevent contact with at least a portion of the annular seal 4 such that when the patient attempts to position an ostomy bag accurately on the attachment 1, an immediate bond between the annular seal 4 a seal on the ostomy bag may be initially avoided. This allows the patient to position the bag accurately, and then, once they are satisfied that it is positioned correctly they can push the bag onto the annular seal 4. This stepwise process reduced or eliminates instances of misalignment leading to reduced waste.

In the embodiment shown in FIG. 3, the lateral protrusion 20 is positioned under the spout-like central section 14. In this arrangement, an inner rim of an opening on an ostomy bag (not shown), which is typically surrounded by the corresponding seal on an ostomy bag, can be easily manoeuvred to rest at the junction between the lateral protrusion 20 and the base of the spout of the central section 14. In this way, the user is able to initially manoeuvre the opening of the ostomy bag over the spout of the central section 14. A positive upward and inward sliding movement of the leading lower edge of the opening of the ostomy bag results in the bag contacting or "landing" on the lateral protrusion 20 which acts to prevent immediate adherence. This arrangement has the advantage of optimally positioning the opening with the lower edge of the opening on the ostomy bag such that the bag is aligned with the underside of the central section 14. Further fine adjustment of the bag is then possible to achieve optimal alignment. Finally, pivoting of the top of the ostomy bag opening towards the attachment then places the seal of the ostomy bag in aligned registry with the annular seal 4 on the ostomy attachment 1 (with or without stabilising elements 16A, 16B therebetween) such that an substantially optimal alignment of the seals is achieved.

The lateral protrusion 20 may be considered to be an embodiment of a stabilising extension 16A, 16B as herein described and may share any or all of the features of a stabilising extension 16A, 16B as described herein.

Reduction in waste in hydrocolloids is important in view of the cost of the material. Increased waste means increased costs for the patient and/or healthcare provider. Waste also derives from current inefficient manufacturing processes for ostomy seals.

In a further aspect of the invention, a multi-part ostomy seal is provided. Ostomy seals are typically provided as an annular ring, broken or unbroken. Without wishing to be bound by theory, it is thought that this arrangement is preferred as users prefer to see a contiguous run of seal material in order to prevent or mitigate leaks once a seal is formed. It has been surprisingly found, however, that there is no need for a contiguous run of seal material under the stoma as once positioned the material, such as hydrocolloid, fuses on contact with itself meaning any initial gaps may be effectively sealed after application. This allows for more cost-effective and efficient methods of manufacture of ostomy seals.

An embodiment of an ostomy seal of an aspect of the present invention is shown in FIG. 5. The annular seal 4 is cut in two parts 22A, 22B, rather than the current standard of cutting the seal as a single annular ring, broken or unbroken. Following cutting from a hydrocolloid roll/sheet. the parts 22A, 22B of hydrocolloid can then be secured together during the manufacturing stage, by a medial practitioner, or by the patient to form the annular seal 4.

Figure 6:
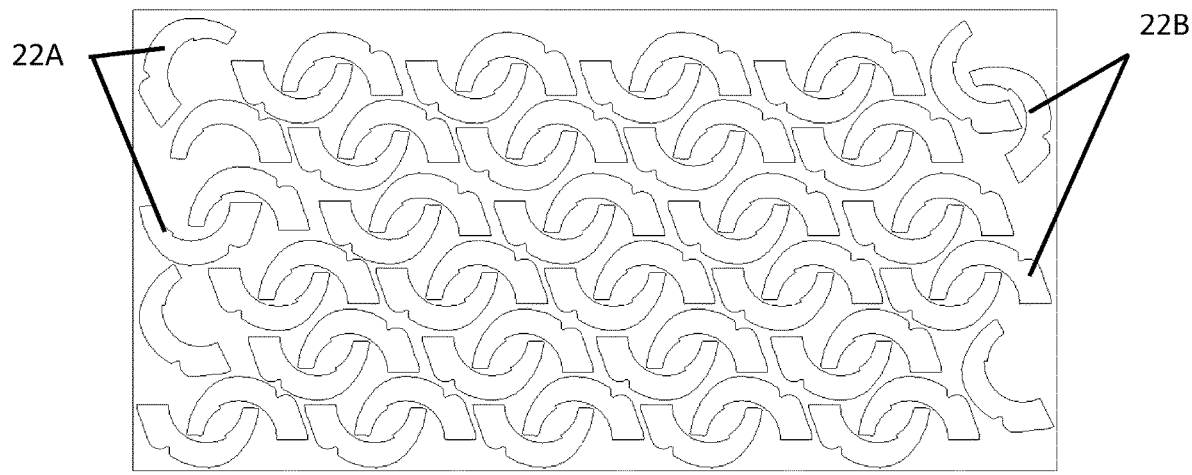
FIG. 6 is a representation of a cutting template in which waste is minimised in accordance with the present invention.
Figure 7:
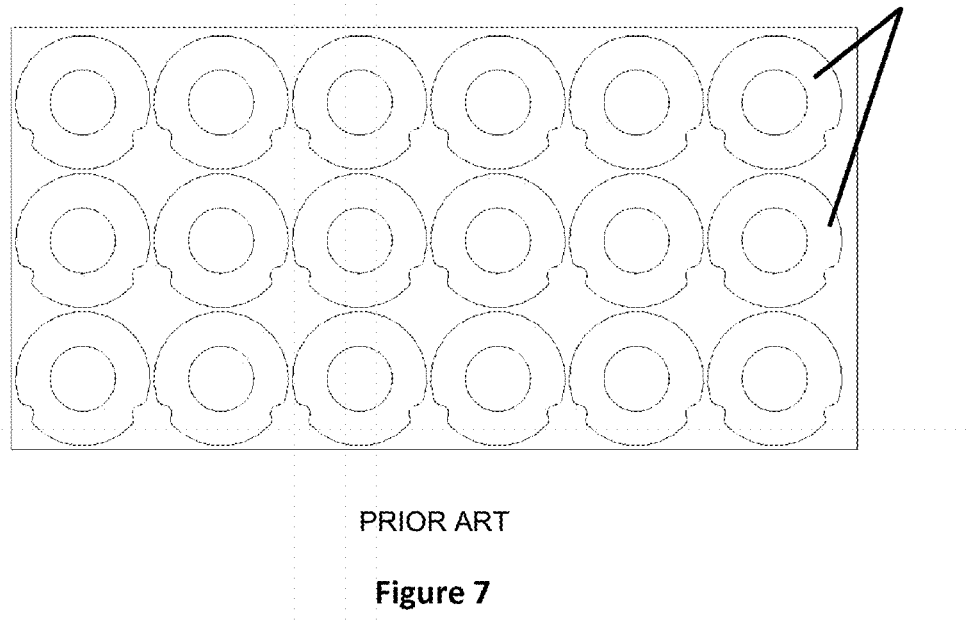
FIG. 7 is a representation of a cutting template of prior art ostomy seals.

As shown in FIG. 6, the parts 22A, 22B can be arranged on a sheet of hydrocolloid such that waste can be reduced compared to the prior art single annular ring 24 design (shown for reference only in FIG. 7). This means that the yield of ostomy products per sheet is greater, which means that each ostomy seal is cheaper to manufacture.

The annular seal may be prepared in two, three, four, five or more parts 22A, 22B. Suitably, the annular seal is prepared in two parts. Suitably the annular seal is prepared in two equal and identical halves to further assist efficiencies in manufacture. The position of at least one if the cuts that separate the annular seal into two halves may be such that extension 15 of the ostomy seal liner of the first aspect of the invention may be positioned therein such that when the material fuses to close the gap between the two halves, a mechanical fixation between the ostomy seal 4 and the ostomy seal liner 2 is also formed.

While the ostomy seal of the aspect of the invention may be prepared in two or more parts, once combined to form a full annular seal is may have one or more of the properties of the ostomy seal 4 described herein.

In embodiments, a percentage increase in sheet yield of between 10% and 60% may be achieved when cutting two half parts 22A, 22B instead of one complete annular seal. Suitably the sheet yield is increased between 20% and 50%. More suitably, the sheet yield is increased between 30% and 50%. Sheet yield in this context is defined as the number of full annular seals produced per sheet (i.e. number of complete annular seals, number of half annular seals divided by two). As a specific example, production of a 34 mm diameter opening product (60 mm outer diameter) allows for a maximum yield of 18 pieces per Vancive sheet if cut in single cut; the same product cut in halves allows for 30 pieces (60 halves) from the same sheet; a yield increase of 40%.

In embodiments the percentage waste reduction in material per sheet for the production of parts 22A, 22B can be between 10% and 60% may be achieved when cutting two half parts 22A, 22B instead of one complete annular seal. Suitably the sheet yield is increased between 20% and 50%. More suitably, the sheet yield is increased between 30% and 50%. Reduction of waste in this context is based on surface area utilised on a full sheet. As a specific example, production of a 34 mm diameter opening product (60 mm outer diameter) compared to the same product cut in halves allows for a percentage waste reduction of 40%.

An additional benefit of this aspect of the present invention is that by having an annular seal 4 that is already separated, the product should be easier to don and can more easily be made to optimally conform to the stoma.

In one aspect, the ostomy seal liner of the present invention with the additional stabilising extensions has the advantage of more securely assembling an ostomy seal liner to an ostomy seal to improve the stability of the ostomy attachment in use. Additionally, by more effectively protecting the absorbent, suitably hydrocolloid, seal material the non-absorbent central or spout section reduces the risk of the hydrocolloid breaking down and thereby improves the longevity of the ostomy seal saving costs for the patient and/or the healthcare provider. Furthermore, the protrusion of the central section, particularly when in the form of a spout, provides a physical barrier that prevents or reduces the stomal output splashing back on the annular seal and/or skin. Finally, the central section, particularly when in the form of a spout, prevents the front face of the bag resting on and at least partially blocking the stoma thereby preventing or reducing the incidence of "pancaking".

In a further aspect, the ostomy seal liner of the present invention has an advantage that the lateral protrusion or "landing pad" can reduce the risk of mis-aligned attachment of the seal between the ostomy attachment and ostomy bag thereby reducing waste.

In another aspect, the ostomy seal of the present invention has an advantage of being manufactured in at least two parts which leads to efficiencies in manufacture and reduction in waste.

It should be understood that the different embodiments of the invention described herein can be combined where appropriate and that features of the embodiments of the invention can be used interchangeably with other embodiments where appropriate.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the scope of the invention as defined by the claims.

The invention claimed is:

1. An ostomy attachment comprising:
a flexible annular seal configured to at least partially surround a stoma, the flexible annular seal comprising a first face and a second face; wherein the first face of the flexible annular seal and the second face of the flexible annular seal are bounded by an inner rim and an outer rim, wherein the inner rim is concentrically arranged within the outer rim; and
an ostomy seal liner configured to engage with the inner rim of the flexible annular seal;
wherein the ostomy seal liner comprises one or more stabilising extensions, wherein the one or more stabilising extensions extend radially outward and over the first face of the flexible annular seal; and wherein the one or more stabilising extensions are in direct contact with the first face of the flexible annular seal to adhere and mechanically fix the flexible annular seal to the ostomy seal liner.

2. The ostomy attachment of claim 1, wherein the one or more stabilising extensions are in continuous direct contact with the first face of the flexible annular seal.

3. The ostomy attachment of claim 1, wherein the inner rim and the outer rim comprise a distance therebetween, and wherein the one or more stabilising extensions extend across the first face of the flexible annular seal by at least 30% of the distance between the inner rim and the outer rim.

4. The ostomy attachment of claim 1, wherein the stabilising extensions are planar.

5. The ostomy attachment of claim 1, wherein the one or more stabilising extensions each comprise one or more apertures or relief areas.

6. The ostomy attachment of claim 1, wherein the flexible annular seal is formed of absorbent material and the ostomy seal liner is formed of non-absorbent material.

7. The ostomy attachment of claim 6, wherein the absorbent material is a hydrocolloid.

8. The ostomy attachment of claim 1, wherein the ostomy seal liner comprises at least one resiliently deformable arm.

9. The ostomy attachment of claim 8, wherein each of the one or more stabilising extensions is positioned at an end of the at least one resiliently deformable arm.

10. The ostomy attachment of claim 8, wherein the ostomy seal liner comprises two resiliently deformable arms.

11. The ostomy attachment of claim 8, wherein the ostomy seal liner further comprises a central section to which the at least one resiliently deformable arm is attached.

12. The ostomy attachment of claim 11, wherein the central section comprises a spout that in use is disposed beneath the stoma and is configured to direct ostomy output away from a patient's skin and into an ostomy bag.

13. The ostomy attachment of claim 12, wherein the spout is angled to optimise collection of the ostomy output and delivery of the ostomy output into the ostomy bag.

14. The ostomy attachment of claim 8, wherein the resiliently deformable arm is attached at both ends to the central section to form an annular ring.

15. The ostomy attachment of claim 14, wherein the one or more stabilising extensions are positioned regularly spaced around a circumference of the annular ring.

16. The ostomy attachment of claim 8, wherein the at least one resiliently deformable arm comprises a length, and wherein the one or more stabilising extensions extend outwardly from no more than 30% of the length of the at least one resiliently deformable arm.

17. The ostomy attachment of claim 1, wherein the ostomy seal liner is fixedly attached to the flexible annular seal.

18. An ostomy seal liner for engaging a flexible annular seal configured to at least partially surround a stoma, the flexible annular seal comprising:
a first face and
a second face, wherein the first face of the flexible annular seal and the second face of the flexible annular seal are bounded by an inner rim and an outer rim, wherein the inner rim is concentrically arranged within the outer rim,
wherein the ostomy seal liner comprises one or more stabilising extensions, wherein the one or more stabilising extensions extend radially outward and over the first face of the flexible annular seal; and wherein the one or more stabilising extensions are in direct contact with the first face of the flexible annular seal to adhere and mechanically fix the flexible annular seal to the ostomy seal liner.

19. An ostomy seal liner for use in the ostomy attachment of claim 1.

\* \* \* \* \*